United States Patent [19]

Smith et al.

[11] Patent Number: 5,118,611
[45] Date of Patent: Jun. 2, 1992

[54] ADENOCARCINOMA ANTIGEN BINDING METHODS AND REAGENTS

[75] Inventors: Lloyd H. Smith, Davis; Nelson N. H. Teng, Hillsborough, both of Calif.

[73] Assignee: Adeza Biomedical Corporation, Sunnyvale, Calif.

[21] Appl. No.: 252,614

[22] Filed: Oct. 3, 1988

Related U.S. Application Data

[63] Continuation-in-part of Ser. No. 223,574, Jul. 25, 1988, abandoned.

[51] Int. Cl.$^5$ ............... G01N 33/574; G01N 33/53; C12N 5/12
[52] U.S. Cl. .................. 435/7.23; 435/240.26; 435/240.27; 435/965; 436/548; 436/64; 436/813; 530/808; 530/809; 530/387.2; 530/388.15; 530/388.85; 530/865
[58] Field of Search ............... 435/7, 240.26, 240.27, 435/7.23, 965; 436/548, 64, 813; 530/387, 808, 809

[56] References Cited

U.S. PATENT DOCUMENTS

| | | | |
|---|---|---|---|
| 4,666,845 | 5/1987 | Mattes et al. | 436/548 |
| 4,800,155 | 1/1990 | Taniguchi et al. | 435/7 |
| 4,816,402 | 3/1989 | Rosen et al. | 435/240 |
| 4,921,790 | 5/1990 | O'Brien | 435/7 |

OTHER PUBLICATIONS

Shitara, K. et al. 1987, Distribution of Lung Adenocarcinoma-associated Antigens in Human Tissues . . . Cancer Research 47 1267.
Hinoda, Y. et al, 1985 Detection of Circulating Adenocarcinoma-associated antigen in Sera Cancer Patients . . . Jpn. J. Can. Res. (Gann) 76/1203.
L. H. Smith et al. 1987, Generation of Human Monoclonal Antibodies to Cancer-Associated Antigens Using Limited Numbers . . . J. Immumolog. Meth. 105 263.
Teng et al., 1983, Construction and Testing of Human--Mouse Heteromyelomas for Human Monoclonal Production, PUAS 80 7308.
Campling et al., 1985, The EBV Hybridoma Technique and Its Application, In Human Hybridomas, Mareel Dekker, Inc., N.Y. pp. 3-22.
Smith L. H. et al.; J of Immunological Methods, 105, (1987) 263-273.
Baumal et al. *Cancer Res.* 46: 3994, 1986.
Bailey et al. *Proc Natl. Acad. Sci. (U.S.A.) 83: 5291, 1986.*
Bhattacharya et al. *Cancerros.* 44: 4528, 1984.

*Primary Examiner*—Esther L. Kepplinger
*Assistant Examiner*—Toni Scheiner
*Attorney, Agent, or Firm*—Skjerven, Mortil, MacPherson, Franklin & Friel

[57] ABSTRACT

Novel adenocarcinoma binding human monoclonal antibody binds preferentially with ADCA antigens and is useful in diagnostic and imaging methods for identifying and locating adenocarcinoma cells, and in therapeutic methods to reduce the reproduction of adenocarcinoma cells. The novel ADCA antigen is useful in methods for diagnosing the presence of adenocarcinoma. The antigen, antibodies, hybridoma, reagents, therapeutic agents and methods of use are aspects of the invention.

11 Claims, No Drawings

ADENOCARCINOMA ANTIGEN BINDING METHODS AND REAGENTS

RELATIONSHIP TO COPENDING APPLICATION

This application is a continuation-in-part of copending application Ser. No. 223,574, filed Jul. 25, 1988, and titled "Adenocarcinoma Antigen Binding Methods and Reagents", now abandoned.

FIELD OF THE INVENTION

This invention relates to diagnostic, imaging and therapeutic methods and associated reagents for cancer markers. In particular, this invention relates to a newly discovered adenocarcinoma antigen marker (ADCA) and to diagnostic, imaging and treatment methods involving preferential antibody binding interactions with the marker.

BACKGROUND OF THE INVENTION

A tumor marker is a biochemical indicator for the presence of a tumor. As used herein, a "tumor marker" refers to a tumor-derived molecule that can be detected in tumor tissue, plasma or other body fluids.

Tumor markers are used in clinical medicine in the diagnosis and mapping of cancer, to determine response to therapy and as an indication of relapse during the follow-up period. Histopathologic diagnosis of cancer can include the immunochemistry techniques developed for detecting tumor markers in tissue biopsies, relying on the use of antibodies which bind preferentially with the marker. In radioimmunoimaging and radiotherapy, radiolabeled or tagged antibodies are used for locating and mapping metastases or delivering lethal irradiation locally to the tumor. These methods rely on the selective binding of antibodies with tumor markers.

Tumor markers which have proven to be clinically useful for cancers include alpha-fetoprotein, carcinoembryonic antigen, human chorionic gonadotropin, calcitonin, prostatic acid phosphatase, CA-125 and immunoglobulins. Each marker has been found useful for certain specific cancers. Newly discovered protein tumor markers include prostate-specific antigen (prostate cancer) and tumor-associated antigen (TA-4) (uterine cervix). In addition, investigations for cancer markers produced by oncogenes have expanded. One limitation of the markers found to date is their presence, at some level, in non-tumor tissues. As a consequence, serum tumor marker panels are suggested for more reliable diagnosis of certain cancers. Another limitation in the current technology is the absence of reliable markers for certain general types of cancers such as adenocarcinomas.

The promise of monoclonal antibodies (MAbs) for improved diagnosis and therapy of cancer is evidenced by a growing number of trials using mouse MAbs to cancer-associated antigens as reagents for serologic diagnosis, imaging and therapy. MAb variable regions possess significant informational content, potentially conferring enhanced selective capability when compared to conventional modes of cancer diagnosis and therapy. However, the in vivo clinical use of mouse MAbs may be limited, since a substantial proportion of patients who have received parenteral mouse MAbs produce an anti-mouse Ig response. Such a response occurs more frequently after multiple administrations, may occur despite immunosuppressive therapy and may result in adverse clinical sequelae as well as abrogation of the intended diagnostic or therapeutic effect. Efforts to reduce the immunogenicity of mouse MAbs include the utilization of antibody fragments or the creation of genetically engineered chimeric human-mouse MAbs.

Human MAbs (hMAbs) would appear to be an attractive solution to the MAb immunogenicity problem. HMAbs have been considered more difficult and costly to generate than mouse MAbs, and relatively few examples of well characterized HMAbs to cancer-associated antigens have been described. Human serologic studies have revealed that a spectrum of types of human cancer-associated antigens are immunogenic, including examples of antigens which are (i) highly specific but only found in individual tumors ("Class I", e.g., idiotypes of B-cell lymphomas), (ii) highly nonspecific antigens also found among many normal tissues ("Class III", e.g., blood group antigens), or (iii) expressed by tumor cells of similar histogenesis but in a restricted or trace distribution among normal cells ("Class II", e.g., differentiation antigens). The reactivity of HMAbs derived from cancer patient lymphocytes appears to recapitulate this spectrum of specificity and suggests that HMAbs of intermediate (Class II) specificity could be produced and utilized to detect antigens shared by cancer cells, but sparingly expressed by normal cells. Although not perfectly specific, such HMAbs could still prove useful for clinical application depending on the distribution of the target antigens among normal tissues.

DESCRIPTION OF THE PRIOR ART

A general survey of the current art in cancer diagnosis and prognosis is provided by Virji, M. et al, *CA-A Cancer Journal for Clinicians.* 38:104-126 (1988) and the publications cited therein. Included are investigations of products of oncogenes detected in some cancers (Virji, pp 116-120) and the suggestion that the detection of oncogene products in plasma or other body fluids may be potentially useful for the detection of oncogene-associated cancers in high-risk groups.

A number of laboratories have reported successful generation of hMAbs to cancer-associated antigens. Cote, R. et al, *Proc.Natl.Acad.Sci., U.S.A.* 83:2959-2963 (1986) reported generating hMAbs which recognized target antigens with a spectrum of specificities from patients with a variety of diseases. Examples of hMAbs to differentiation-type antigens with restricted distribution among normal tissues (Class II), yet expression by multiple human cancer cell lines, were clearly recovered. Others have reported generation of human MAbs which selectively recognize antigens associated with melanoma (Kan-Mitchell, J. et al, *Cancer Res.* 46:2490.2496 (1986)), leukemia (Olsson, L. et al, *J.Exp.Med.* 159:537-550 (1984)), or cancers of the breast (Schlom, J. et al, *Proc.Natl.Acad.Sci., U.S.A.* 77:6841-6845 (1980)), colon (Haspel, M. et al, *Cancer Res.* 45:3951-3961 (1985)) and Borup-Christensen, P. et al, *Int.J.Cancer.* 37:683-688 (1986)), prostate (Lowe, D et al, *J. Urol.* 132:780-785 (1984)), cervix (Hagiwara, H. et al, *Mol.Biol.Med.* 1:245-252 (1983)) and vulva (Glassy, M. *Cancer Res.* 47:5181-5188 (1987)). Glassy has described a human IgG MAb (VLN3G2) recovered from a patient with vulvar carcinoma which recognizes an antigen present on many human cancer cell lines including an epidermoid carcinoma of the vulva. In immunoprecipitation, VLN 3G2 recognizes a polypeptide of 48 kD. Although this antigen possesses a molecular weight in a range similar to that of the ADCA antigen of this invention, ADCA antibody was not found to react with three different squamous cell cancers of the vulva.

Borup-Christensen, P. et al, "UCLA symposia on molecular & cellular biology," *J. Cellular Biochemistry.* Supp. 12E, 1988, p 136 (T204) (Apr. 17-30, 1988) and Erb, K. et al, "UCLA symposia on molecular & cellular biology," *J. Cellular Biochemistry.* Supp. 12E, 1988, p 137 (T204) (Apr. 17-30, 1988) report three hMAbs from lymph nodes draining colorectal cancer which bind to cancer-associated antigens. G4146 bound to two components of colon cancer cells of 59 kD and 61 kD, B9165 bound to one component of 43 kD, F11348 bound to several components from 30 kD to 300 kD. The B9165 hMAb was an IgM antibody reactive with antigen associated with adenocarcinomas, preferentially endodermally derived epithelium tissues such as colorectal cancer, mammary cancer and ovarian cancer, while normal tissue binding was restricted to mammary and prostate epithelium.

L. H. Smith, A. Yin, M. Bieber and N. N. H. Teng *J.Immun.Methods.* 105:263-273 (1987) reported generation of hMAbs to ovarian cancer-associated antigens using patient lymphocytes and the heteromyeloma fusion partner SHM-D33 (U.S. Pat. No. 4,574,116). Among the hMAbs listed was MS2B6 which we have found to bind with the ADCA antigen.

Of the dozens of mouse MAbs to cancer-associated antigens which have been reported, many also recognize antigens associated with ovarian cancer, and some of these antigens share certain characteristics with the ADCA antigen. Cancer-associated antigens Ca125 (Davis. H. et al. *Cancer Res.* 46:6143-6148 (1986)), TAG-72 (Johnson. V. et al. *Cancer Res.* 46:850-857 (1986)), DF3 antigen (Friedman, E. et al. *Cancer Res.* 46:5189-5194 (1986)), HMFG-2 (Burchell, J. et al, *J.Immol.* 131:508-513 (1983)), F 36/22 antigen (Croghan, G. et al, *Cancer Res.* 44:1954-1962 (1984)), SGA (de Krester, T. et al. *Int.J.Cancer.* 37:705-712 (1986)), MO,2 antigen (Miotti, S. et al. *Cancer Res.* 45:826-832 (1985)), ID3 antigen (Gangopadhyay, A. et al, *Cancer Res.* 45:1744-1752 (1985)) and Du-Pan-2 antigen (Lan, M. et al. *Cancer Res.* 45:305-310 (1985)) are all most often found in association with epithelial ovarian cancer. However, these antigens are all high molecular weight glycoproteins or mucins and thus differ from the ADCA structure. As noted above, ADCA has been shown not to compete for the Ca125 epitope.

Several ovarian cancer-associated antigens have been detected by mouse monoclonal antibodies which do have similar molecular size characteristics of the ADCA antigen. Bhattacharya, M. et al, *Cancer Res.* 44:4528-4534 (1984) described antigen gp48, a 48 kD glycoprotein associated with ovarian epithelial cancers and other adenocarcinomas, and also present in normal cervix and colon. Unlike the ADCA antigen, gp48 could be detected in formalin-sized deparaffinized tissue sections. The same group (Bhattacharya, M. et al, *Hybridoma.* 4:153-162 (1985)) have described a 60 kD glycoprotein associated with ovarian cancer also detected in deparaffinized sections and present in normal lung alveoli, as well as liver.

Miotti, S. et al, *Int.J.Cancer.* 39:297-303 (1987) have characterized two ovarian cancer associated antigens of 48-50 kD and 38-40 kD These antigens could not be detected in deparaffinized tissues, like ADCA requiring frozen sections for immunohistologic analysis. The 48-50 kD species was detected in normal breast, pancreas, kidney and prostate, but the 38-40 kD antigen was not detectable in normal tissues. However, unlike the ADCA antigen, these antigens were absent from the mucinous ovarian cancers examined and could only be analyzed by immunoprecipitation, antigen activity being lost by boiling in SDS sample buffer.

Mattes, M. et al in *Proc.Natl.Acad.Sci., U.S.A.* 81:568-572 (1984), *Hybridoma.* 2:253-264 (1983), and *Cancer Res.* 47:6741-6750 (1987) have conducted a systematic study of mouse MAbs generated against ovarian cancer cell lines and ascites tumor cells. Of the many MAbs analyzed, MH99 and MW207 recognize target antigens sharing characteristics with the ADCA antigen. Structurally, the MH99 antigen has two apparently disulfide-bonded subunits which appear in immunoblots as 38 kD and 29 kD bands. The MW 207 antigen has only a 37 kD band. The MW207 antigen has only a 37 kD band. The MW207 antigen was detected in normal epithelia of bronchus, lung, kidney, pancreas, thyroid, endometrium, fallopian tube, endocervix and breast, but was absent in mesothelial cells. Unlike the ADCA antigen, however, MW207 antigenic activity was destroyed by reducing conditions.

Moldenhauer, G. et al, *British.J.Cancer.* 56:714-721 (1987) reported an epithelium-specific surface glycoprotein of 34 kD cancer marker which was immunoprecipitated with a mouse MAb HEA125. Based on reports that the antibody did not significantly discriminate between different histotypes of carcinoma or show organ specificity, the epitope would appear to be widely distributed and have a very different distribution from the ADCA antigen of this invention.

Tsuji, Y. et al, Cancer Res. 45:2358-2362 (1985a) report mouse MAbs 4C7 derived from a mucinous carcinoma line OVA-1 and 3C2 obtained from a serous carcinoma line HOC-21 and binding with two different surface epitopes of human ovarian epithelial carcinomas. The distribution of binding by these MAbs does not correspond to the ADCA epitope distribution.

U.S. Pat. No. 4,145,336 describes isomeric species of carcinoembryonic antigen (CEA). This has a molecular weight of 180-200 kD, clearly differing from the ADCA structure which has a major component molecular weight of 38 kD.

U.S. Pat. No. 4,584,278 describes a method for purifying NB/70K isolated from ovarian tissue, showing it to be as single band at 70 kD in SDS-PAGE. U.S. Pat. No. 4,713,351 describes assays and MAbs for antigen NB/70K. On the basis of molecular structure, NB/70K differs from ADCA.

U.S. Pat. No. 4,666,845 describes a number of cancer antigens. Lipid antigen MD144, present in chloroform-:methanol extracts of ovarian cancer cell line 2774, migrated at the dye front in acrylamide gels. ADCA is very different based on SDS-PAGE Western blot analysis of ADCA, and MS2B6 MAb did not bind to lipid extracts. MA55 failed to react in tissue sections, clearly different from ADCA. MF61 is also a lipid antigen, and additionally is present in thyroid colloid, unlike ADCA. MF116 is a 105 kD glycoprotein, inactivated by heating at 100° C. Also unlike ADCA, the antigen was not detected by immunoperoxidase examination of tissue specimens. MH94 was present in sebaceous glands of skin, but ADCA was found to be present only in sweat ducts epithelia in skin.

European patent applications EP 86309515.4 and EP 86309516.2 disclose MAbs 2G3, 120H7, 200F9, 204F4, 245E7, 369FIO, 788G6 and 871E3, all recognizing high molecular weight mucin antigens and therefore not ADCA. Similarly, MAbs 9C6 (75 kD), 33F8 (66 kD), 260F9 (55 kD), 266B2 (55 kD), 451C3 (95 kD), 454A12 (95 kD) and 454CII (200 kD) had antigen structures which differed significantly from ADCA. MAb 44F4 bound to several antigens including a 39 kD antigen, but as shown in Table 2, it bound to normal granulocytes, unlike ADCA. MAbs 317G5 and 650 E2 both recognize a 42 kD antigen, similar in size to the ADCA antigen, but unlike ADCA, these MAbs bind antigen present in normal liver (Table I). MAb 650E2 also bound to lung ascini whereas MS2B6 MAb bound only to bronchial epithelium. MAbs 44B2, 219F3, 280DII, 388D4 and 421E8 have no antigen molecular weight assignments but are distinct from ADCA on the basis of tissue distribution, the following being differences from ADCA: 44B2 (esophagus, liver); 219F3 (lymphoma, esophagus, hair follicles, lymphocytes); 280DII (lymphoma, granulocytes, esophagus, liver, hair follicles, skin epithelium, lymphocytes); and 388D4 (melanoma, esophagus, skin epithelium, sebaceous glands).

SUMMARY OF THE INVENTION

The method of this invention for determining the presence of adenocarcinoma having an ADCA antigen epitope in a patient comprises contacting a sample from the patient with an ADCA binding antibody and determining binding of the antibody with a component of the sample. The sample can be a fluid sample, such as a blood serum sample, or a tissue sample. The antibody can be a human monoclonal antibody such as the MS2B6 IgM antibody.

A method of this invention for determining the presence of adenocarcinoma having an ADCA antigen epitope in a patient comprises contacting a blood serum sample from the patient with ADCA antigen or ADCA antiidiotype antibody and determining binding of ADCA antigen or ADCA antiidiotype antibody with antibody in the sample.

A method of this invention for determining the presence of adenocarcinoma having an ADCA antigen epitope in a patient comprises contacting a blood serum sample from the patient with ADCA binding antibody, and determining binding of ADCA binding antibody with ADCA antigen in the sample.

A method of this invention for imaging adenocarcinoma comprises delivering ADCA binding antibody to tissue in the body suspected of being an adenocarcinoma, the antibody being bound to a label which has a distinctive property from which an image can be derived, and obtaining an image from the area of the body having the tissue. In this method, the the antibody can be a human monoclonal antibody such as the MS2B6 IgM. The tissue can be ovarian or non-ovarian tissue having the ADCA antigen epitope. The label can be a radiolabel, and the image can be derived from a detection of radiation from the body area containing the tissue suspected of being an adenocarcinoma. Alternatively, the label can be a paramagnetic contrast label and the image can be derived by NMR measurements of the body area containing the tissue suspected of being an adenocarcinoma.

A method of this invention for radiotherapy of adenocarcinoma having an ADCA antigen epitope comprises delivering ADCA binding antibody to adenocarcinoma tissue, the antibody being bound to a therapeutic moiety which alone or in conjunction with secondary treatment is useful in reducing the reproduction of adenocarcinoma cells. In one aspect of this method, the therapeutic moiety radiates the adenocarcinoma cells to which it is bound. In another, the therapeutic moiety is a cytotoxic or cytostatic agent or the therapeutic moiety acts to generate a cytotoxic or cytostatic agent when acted upon by a second agent or by radiation.

Also included in this invention are the MS2B6 hybridoma; antibodies which bind preferentially with ADCA antigen, including human monoclonal antibodies such as the MS2B6 IgM antibody; and the ADCA antigen. This invention also includes ADCA binding antibodies conjugated to an imaging moiety such as a radiolabel or NMR contrast label, to a therapeutic moiety such as a cytotoxic or cytotoxic agent, and to an agent which acts to generate a cytotoxic or cytostatic agent when acted upon by a second agent or by radiation. This invention also includes the above agents and reagents in diagnostic, imaging, and therapeutic kit modalities wherein one or more of the agents are contained in vials or other packages.

DETAILED DESCRIPTION OF THE INVENTION

ADCA antigen is an antigen of epithelial differentiation which is expressed by some fetal tissues and persists in adult epithelia of the fallopian tube, endometrium endocervix, colon, bronchus, breast, sweat duct and large renal ducts. It is notably absent from peritoneal mesothelial cells, blood-borne cells or tissue stroma cells. The ADCA antigen is expressed by epithelial ovarian cancer cells, as well as a large proportion of nonovarian adenocarcinomas, but has not been found to be associated with squamous cell cancer, sarcoma, melanoma, lymphoma or malignant germ cell tumors. The target epitope ADCA resides on polypeptides of 38, 44 and 60 kD, and probably does not involve sialic acid resides or glycolipid structures. The binding of MS2B6 IgM to viable ovarian cancer cells, the protease-sensitive nature of such binding, and the distribution of the antigen as revealed by immunoperoxidase studies, suggest that a significant portion of the ADCA antigen is located on the cell surface. At least in the patient of origin, the existence of the human MAb MS2B6 IgM establishes that is target antigen can be immunogenic in humans.

The term "ADCA binding antibody" is defined to include monoclonal and polyclonal antibodies derived from any species which bind preferentially with the ADCA antigen.

The term "antibody" as used herein is defined to include antibodies of classes IgG, IgM, IgA, IgD, and IgE, and fragments, half-antibodies, and hybrid derivatives of antibodies including Fab, and F(ab')$_2$ fragments of antibodies. Antibodies may be polyclonal or monoclonal. Generally, monoclonal antibodies are preferred for use in the methods of this invention. The MS2B6 hMAb is an IgM class antibody.

The term "ADCA antiidiotype antibody" as used herein is defined to be an antiidiotype antibody which will specifically bind with the ADCA antibody and will compete for binding with the ADCA antigen for binding with the ADCA antibody.

Derivation of hybridoma MS2B6 (ATCC HB 9765) is described by Smith, L. et al, *J.Immunol.Methods.* 105:263-273 (1987), the entire contents of which are hereby incorporated by reference. MS2B6 IgM antibody is produced from this hybridoma in serum-free medium and purified by conventional procedures such as are described by Goding, J. MONOCLONAL ANTIBODIES: PRINCIPLES AND PRACTICE. New York: Academic Press pp 98-118 (1983), the entire contents of this book and the references cited therein being hereby incorporated by reference in their entireties.

The antibody fragments can be made by conventional procedures. The MS2B6 hMAb can be fragmented to produce Fab fragments by proteolytic fragmentation procedures as described by Goding, J. (supra, pp 123-124). Fragmentation of MAbs from the ADCA antigen can be carried out by proteolytic methods to yield Fab and F(ab')₂ fragments as described by Goding, J. (supra, pp 118-123).

The ADCA antigen was initially isolated by gel electrophoresis using the SDS-PAGE procedure. Larger quantities of the antigen can be obtained by affinity chromatography of extracts of ovarian cancer tissue which has been extracted with neutral detergent, using MS2B6 hMAb bound to conventional affinity column materials. The treatment of the tissue extract with the column and the elution of the the ADCA antigen from the column can be effected by conventional procedures. Suitable procedures for extracting and purifying proteins are described by Davis, H. et al (supra), Johnson, V. et al (supra) and Friedman, E. (supra), the entire contents of which are hereby incorporated by reference in their entireties.

The polyclonal antibodies can be prepared by conventional procedures, with any mammal used for polyclonal antibody production. Generally a rabbit, guinea pig or goat is adequate. In producing the antibody, a predetermined amount of ADCA antigen is diluted with a physiological saline solution in a suitable concentration. This diluted solution is further diluted by mixing it with a complete Freund's adjuvant to prepare an emulsion. The suspension is then administered to the mammal. For example, the suspension can be administered by intraperitoneal, intramuscular or subcutaneous routes to a rabbit in an amount of 0.05 to a maximum, non-lethal dose which might be as high as 5 mg of the antigen in every administration, and the administration can be continued every other week for 2 to 10 months. Blood is removed from the mammal when the antibody titer is sufficiently elevated, generally one to 2 weeks after the last challenge administration of the suspension. The blood taken from the animal is treated by centrifugal separation to separate the serum containing the antibody.

The polyclonal antibody serum is then affinity purified using conventional affinity chromatography techniques such as those described by Mishell and Shilgi in SELECTED METHODS IN CELLULAR IMMUNOLOGY. San Francisco: Freeman (1980), the entire contents of which are hereby incorporated by reference. Suitable absorbents for use in affinity chromatography include cross-linked agarose and cross-linked polyacrylamides to which the MS2B6 IgM antibody is covalently bonded.

In these procedures, the antibody solution can be applied to the column in a phosphate buffered saline solution, and the antibodies can be eluted with a 2.5M NaSCN solution, pH 8.0. Antibody concentration, if desired, can be achieved by negative pressure dialysis or ultrafiltration. The antibody solution is stable at temperature of 4° C. or less.

Non-human monoclonal antibodies of this invention can be made from the ADCA antigen, purified as described above, are prepared by conventional procedures, generally following the method of Kohler and Milstein, Nature. 256:495-497 (1975). More recent developments are reviewed in Goding, J. (supra, pp 56-97). In general, the hybridoma is prepared by immunizing mice or rats with the ADCA. While female A/J mice (H-2a haplotype, Jackson Laboratories, Bar Harbor, Me.) are preferred, it is contemplated that other mice or rat strains can be used. The immunization schedule and concentration of antigen in the suspension should be such as to produce useful quantities of suitably primed splenocytes and/or lymphocytes. The suspended spleen cells are fused with mouse or rat myeloma cells from a suitable cell line by the use of a suitable fusion promoter. This can be either Sendai Virus, polyethylene glycol or an electrical field. Many mouse myeloma cell lines are known and available, generally from members of the academic community and various deposit banks such as the American Type Culture Collection, Rockville, Md. Balb/C myeloma cells lines are preferred. The myeloma cell line used should preferably be medium sensitive so that unfused myeloma cells will not survive in a selective medium, while hybrids will survive. The most common class is 8-azaguanine resistant cell lines, which lack the enzyme hypoxanthine guanine phosphoribosyl transferase and hence will not be supported by HAT (hypoxanthine, aminopterin, and thymidine) medium. It is also generally preferred that the myeloma cell line used be of the so-called "non-secreting" type, in that it does not produce any antibody, although secreting types may be used. While the preferred fusion promoter is polyethylene glycol having an average molecular weight from about 1000 to 4000 (commercially available as PEG 1000, etc.), other fusion promoters known in the art can be used.

The supernatant in each container (well) containing a hybridoma is then examined for the presence of antibody which binds selectively with ADCA. Procedures suitable for screening are described by Goding, J. W. (supra, pp 72-84). One particular suitable method involves a competition between an anti-mouse immunoglobulin bound to an insoluble support such as a microtiter tray well and a mixture of labeled ADCA and culture supernatant, or between an insolubilized anti-mouse immunoglobulin and a mixture of labeled ADCA and culture supernatant, the amount of label bound to the insoluble support being read to determine the binding of supernatant with the antibodies in the culture supernatant. Another suitable procedure comprises the application of the culture supernatant in a dot to a layer of nitrocellulose paper to which the selected isotype is adhered, rinsing the paper'layer, contacting the paper layer with a chromogen labeled antibody or fluorescent labeled antibody which will bind to the Fc portion of any antibodies bound to paper layer, rinsing the paper layer to remove unbound labeled antibody, and examining the paper layer to determine if bound chromogen or fluorogen is evident where the dot was applied. Automatic tray readers can be used to quickly identify the wells having hybridomas yielding antibodies which bind to the proteins adhered to the insoluble surface.

After the desired hybridomas have been selected and cloned, the resultant antibody can be produced by in vitro culturing in a suitable medium followed by recovery of the antibody from the supernatant. Alternatively, the hybridoma can be injected into mice, preferably syngenic or semisyngenic mice. The hybridoma will cause formation of antibody producing tumors after a suitable incubation time. These will produce a high concentration of the desired antibody (about 5–20 mg/mL) in the bloodstream and peritoneal exudate (ascites) of the host mouse. Although the host mice will also have normal antibodies in their-blood and ascites, the concentration of the normal antibodies will be only about 5 percent of the concentration of the desired monoclonal antibody.

The antibodies and antigens of this invention can be coupled with a variety of moieties useful for diagnostic, imaging and therapeutic methods. In general, procedures suitable for binding such diagnostic labeling moieties to antibodies (described below) can also be used for binding the moieties to the ADCA antigen for immunodiagnostic purposes.

The ADCA antiidiotype antibodies can be prepared from the ADCA antigen as described by Chen, P. et al, J.Exp.Med. 162:487–500 (1985), and in PTC Application No. 8502909 and EP Application No. 141783. Monoclonal antiidiotype antibodies to the ADCA antigen can be prepared by the procedures described in U.S. Pat. No. 4,513,088.

Polyclonal antiidiotype antibodies can be prepared by passing the animal serum obtained by immunizing with ADCA antigen through a column to which MS2B6 hMAb antibody has been covalently bonded by conventional procedures well known in the art. After rinsing to remove residual serum, the column is eluted with a suitable buffer such as sodium acetate buffer to remove the antiidiotype antibody which has been separated, and the eluate is purified by dialysis to remove small molecules in a conventional manner.

Monoclonal antiidiotype antibodies can be prepared by screening the clones from the hybridized spleen cells of mice immunized with purified ADCA antigen or with MS2B6 hMAb antibodies, and screening the wells for clones producing antibodies binding with the MS2B6 hMAb. MS2B6 hMAb bound to a microwell is incubated with hybridoma supernatant for a time sufficient to permit antibody-antigen binding to occur, the supernatant is removed from the well, and the well is rinsed. The well is then incubated with enzyme labeled goat or rabbit anti-Ig or anti-IgM antibody for a time sufficient to permit antibody-antigen binding to occur and the residue is removed from the well by rinsing. A substrate yielding a chromophore or fluorophore in the presence of the enzyme is then added to the well, and the presence the chromophore or fluorophore is used as a criterion for selecting clones. Control wells with irrelevant IgM must also be tested. Only antibodies having activity against MS2B6 hMAb and not irrelevant human MAb are antiidiotype candidates. Preferably, they should be selected to inhibit or compete with MS2B6 MAb binding with ADCA antigen.

Radiolabeled antibodies of this invention can be used for in vitro diagnostic tests. The specific activity of a tagged antibody depends upon the half-life, isotopic purity of the radioactive label and how the label is incorporated into the antibody. Table A lists several commonly used isotopes, their specific activities and half-lives. In immunoassay tests, the higher the specific activity, in general, the better the sensitivity.

TABLE A

| Isotope | Specific Activity of Pure Isotope (Curies/mole) | Half-Life |
|---|---|---|
| $^{14}C$ | $6.25 \times 10^1$ | 5720 years |
| $^3H$ | $2.91 \times 10^4$ | 12.5 years |
| $^{35}S$ | $1.50 \times 10^6$ | 87 days |
| $^{125}I$ | $2.18 \times 10^6$ | 60 days |
| $^{32}P$ | $3.16 \times 10^6$ | 14.3 days |
| $^{131}I$ | $1.62 \times 10^7$ | 8.1 days |

Procedures for labeling antibodies with radioactive isotopes listed in Table A are generally known in the art. Tritium labeling procedures are described in U.S. Pat. No. 4,302,438, for example. Iodinating, tritium labeling and $^{35}S$ labeling procedures especially adapted for murine monoclonal antibodies are described by Goding, J. W. (supra, pp 124–126) and the references cited therein. Other procedures for iodinating antibodies are described by Hunter and Greenwood, Nature. 144:945 (1962) and David et al, Biochemistry. 13:1014–1021 (1974) and in U.S. Pat. Nos. 3,867,517 and 4,376,110.

Radiolabeled antibodies can be also be used for imaging and radiotherapy. Radiolabeling elements which are useful in imaging include $^{123}I$, $^{131}I$, $^{111}In$, and $^{99m}Tc$, for example. Procedures for iodinating antibodies are described by Greenwood, F. et al, Biochem.J. 89:114–123 (1963); Marchalonis, J. Biochem.J. 113:299–305 (1969); and Morrison, M. et al, Immunochemistry. 289–297 (1971). Procedures for $^{99m}Tc$-labeling are described by Rhodes, B. et al. in Burchiel, S. et al (eds.), TUMOR IMAGING: THE RADIOIMMUNOCHEMICAL DETECTION OF CANCER. New York: Masson 111–123 (1982), and the references cited therein. Procedures suitable for $^{111}In$-labeling antibodies are described by Hnatowich, D. J. et al, J.Immul.Methods. 65:147–157 (1983); Hnatowich, D. J. et al, Science. 220:613–615 (1983), Hnatowich, D. et al, J. Applied Radiation. 35:554–557 (1984), and Buckley, R. G. et al, F.E.B.S. 166:202–204 (1984).

Cytotoxic radiopharmaceuticals for treating ovarian cancer can be prepared by conjugating high linear energy transfer emitting isotopes (e.g., Y, Pr) to the antibodies. Ions of these materials can be incorporated as chelates using DTPA or other chelates coupled to the antibodies.

Antibodies labeled with enzymes are useful for in vitro diagnostic tests. Examples of suitable systems, coupling procedures and substrate reactions therewith are disclosed in U.S. Pat. Nos. Re. 31,006, 3,654,090, 4,214,048, 4,289,747, 4,302,438, 4,312,943, 4,376,110 and the references cited therein, for example. Examples of other suitable systems are described by Pesce et al, Clin.Chem. 20:353–359 (1974) and Wisdom, G., Clin.-Chem. 22:1243 (1976).

A list of suitable enzyme classes and specific examples for each class are shown in Table B.

TABLE B

| Class | Enzyme Example |
|---|---|
| Hydrolases | Amylases |
| Nucleases | Polynucleotidase |
| Amidases | Arginase |
| Purine deaminases | Adenase |
| Peptidases | Aminopolypeptidase |
| Proteinases | Pepsin |
| Esterases | Lipases |
| Iron Enzymes | Catalase |
| Copper Enzymes | Tyrosinases |

TABLE B-continued

| Class | Enzyme Example |
|---|---|
| Enzymes containing Coenzymes | Alcohol dehydrogenase |
| Enzymes reducing cytochrome | Succinic dehydrogenase |
| Yellow enzymes | Diaphorase |
| Mutases | Glyoxalase |
| Desmolases | Aldolase |
| Oxidases | Glucose oxidase |
|  | Horseradish peroxidase |
| Phosphatases | Alkaline Phosphatases |
|  | Acid Phosphatases |
| Dehydrogenases | G6PDH (Glucose 6 phosphodehydrogenase) |
| β-galactosidase |  |
| Phosphorylases |  |
| Hexokinases |  |

A list of suitable enzymes are described in Hawk, et al. PRACTICAL PHYSIOLOGICAL CHEMISTRY, New York: McGraw-Hill pp 306-397 (1954).

Fluorogenic and chromogenic enzymes (enzymes in the presence of which a selected substrate will produce a fluorescent or chromogenic product) are useful labeling moieties. Methods for selectively conjugating enzymes to antibodies without impairing the ability of the antibody to bind with antigen and for conjugating enzymes to proteinaceous reagents are well known in the art.

Suitable enzymes and procedures for coupling them to antibodies are described by Ichiro Chibata in IMMOBILIZED ENZYMES (supra); A. Cuatrecasas, *J.Bio.-Chem.* 245:(1970) Wilson, M. et al, INTERNATIONAL CONFERENCE IN IMMUNOFLUORESCENCE AND RELATED STAINING TECHNIQUES. W. Knapp et al, editors. Amsterdam: Elsevier pp 215-244 (1978); Sullivan, M. et al, *Annals of Clinical Biochemistry.* 16:221-240 (1979); Nygren, H. et al. *Medical Biology.* 57:187-191 (1979); Gadkari, D. et al, *Journal of Virological Methods.* 10:215-224 (1985); Tijssen, P. et al, *Analytical Biochemistry.* 136:551-457 (1984); Tsuruta, J. et al, *The Journal of Histochemistry and Cytochemistry.* 33:767-777 (1985); Ishikawa, E., *Journal of Immunoassay.* 4:209-327 (1983); and in U.S. Pat. No. 4,190,496, for example, the entire contents of the above listed references being hereby incorporated by reference in their entireties.

The preferred enzymes and suitable substrates corresponding thereto include horseradish peroxidase for which suitable substrates are o-phenylenediamine, m-phenylenediamine, o-dianisidine, and 4-chloro-α-napthol. They also include β-galactosidase for which suitable substrates are 4-methylumbelliferyl-β-D-galactoside, p-nitrophenyl-β-D-galactose, p-nitrophenol, o-nitrophenyl-β-D-galactose, and o-nitrophenol, for example. They include alkaline phosphatase for which suitable substrates are p-nitrophenylphosphate, indoxyl phosphate, and 5-bromo-3-chloroindoxyl phosphate, for example.

Examples of suitable procedures for enzyme labeling the antibody include the use of carbodiimides, dialdehydes, and gluteraldehyde bifunctional coupling reagents. Linkage of enzymes through amine groups can be achieved by treating the proteins with thionyl chloride, N-hydroxysuccinimide or similar reagents in an anhydrous solvent such as dimethylformamide, dioxane, dimethylsulfoxide, tetrahydrofuran, or the like. Alternative coupling agents include carbodiimides such as 1-ethyl-3-(3-(N,N'-dimethylamino)propyl)-carbodiimide, 1-cyclohexyl-3-(2-morpholinoethyl)carbodiimide methyl-p-toluenesulfonate, succinimidyl 4-(N-maleimidoethyl)-cyclohexane-1-carboxylate, and succinimidyl 3-(2-pyridyldithio)-propionate, for example.

The carbohydrate moiety of an enzyme can also be oxidized to an aldehyde and reacted with lysyl amino groups of immunoglobulins to form a Schiff's base. Reduction with sodium borohydride effects a stable linkage of enzyme and antibody. Horseradish peroxidase with antibody can be efficiently linked to immunoglobulins by the method of Wilson, supra.

Fluorophore and chromophore labeled antibodies can be prepared from standard moieties known in the art. Since antibodies and other proteins absorb light having wavelengths up to about 310 nm, the fluorescent moieties should be selected to have substantial absorption at wavelengths above 310 nm and preferably above 400 nm. A variety of suitable fluorescers and chromophores are described by Stryer, *Science.* 162:526 (1968) and Brand, L. et al, *Annual Review of Biochemistry.* 41:843-868 (1972). The antibodies can be labeled with fluorescent chromophore groups by conventional procedures such as those disclosed in U.S. Pat. Nos. 3,940,475, 4,289,747 and 4,376,110, for example.

One group of fluorescers having a number of the desirable properties described above are the xanthene dyes, which include the fluoresceins derived from 3,6-dihydroxy-9-phenylxanthhydrol and resamines and rhodamines derived from 3,6-diamino-9-phenylxanthydrol and lissanime rhodamine B. The rhodamine and fluorescein derivatives of 9-o-carboxyphenylxanthhydrol have a 9-o-carboxyphenyl group. Fluorescein compounds having reactive coupling groups such as amino and isothiocyanate groups such as fluorescein isothiocyanate and fluorescamine are readily available. Another group of fluorescent compounds are the naphthylamines, having an amino group in the α or β position.

Antibodies can be labeled with fluorochromes or chromophores by the procedures described by Goding, J. (supra, pp 208-249).

The antibodies used in the methods of this invention can be covalently bonded to avidin or biotin in one embodiment of this invention. Suitable binding procedures involve cross-linking through a bifunctional cross-linking agent. Suitable bifunctional compounds are described by Peters, K. et al. *Ann.Rev.Biochim.* 46:523 (1977).

In other instances, the bonds can be formed directly between the reagents themselves. For example, antibody can be bound to avidin through functional groups on the respective materials. As a specific example, avidin can be treated with periodate and reacted with antibody to give a Schiff base formation without inhibiting the biotin to avidin binding or blocking immunological activity of the antibody.

Known techniques using bifunctional cross-linking agents include the following: (a) a one-step glutaraldehyde linkage, Avrameas, S., *Immunochemistry.* 6:43 (1969); (b) two-step glutaraldehyde linkage, Avrameas, S., *Immunochemistry.* 8:1175 (1971); and (c) dimaleimide linkage, Kato, K. et al, *Euro.J.Biochem.* 62:285 (1966).

Tumor specific ADCA antibodies of this invention can also be used to deliver therapeutic compounds and elements to adenocarcinoma cells. The drugs can be cytotoxic moieties or enzymatically active toxins of bacterial, fungal or plant origin, or an enzymatically active polypeptide chain or fragment "A chain" of such a toxin. Enzymatically active toxins and fragments thereof are exemplified by diphtheria toxin A fragment, nonbinding active fragments of diptheria toxin, exotoxin A (from *Pseudomonas aeruginosa*), ricin A chain, abrin A chain, modeccin A chain, α-sarcin, certain *Aleurites fordii* proteins, certain Dianthin proteins, *Phytolacca americana* proteins (PAP, PAPII and PAP-S), *Morodica charantia* inhibitor, curcin, crotin, *Saponaria officinalis* inhibitor, gelonin, mitogellin, restrictocin, phenomycin, and enomycin, for example. Procedures for preparing enzymatically active polypeptides of the immunotoxins are described in PCT W084/03508 AND PCT W085/03508. Certain cytotoxic moieties are derived from adriamycin, chlorambucil, daunomycin, methotrexate, neocarzinostatin and platinum, for example.

Procedures for conjugating the antibodies with the cytotoxic agents have been previously described. Procedures for conjugating chlorambucil with antibodies are described by Flechner, I. *European Journal of Cancer.* 9:741-745 (1973); Ghose, T. et al, *British Medical Journal.* 3:495-499 (1972); and Szekerke, M., et al, *Neoplasma.* 19:211-215 (1972). Procedures for conjugating daunomycin and adriamycin to antibodies are described by Hurwitz, E. et al, *Cancer Research.* 35:1175-1181 (1975) and Arnon, R. et al. *Cancer Surveys.* 1:429-449 (1982). Procedures for preparing antibody-ricin conjugates are described in U.S. Pat. No. 4,414,148 and by Osawa, T. et al, *Cancer Surveys.* 1:353-372 (1982). Procedures for preparing antibody-toxin A (diphtheria toxin) conjugates are described in Martinez, O. et al, *Cancer Surveys.* 1:373-388 (1982) and the references cited therein. Coupling procedures as also described in EP 86309516.2.

Antibodies can also be coupled with photocytotoxic agents such as porphyrins such as hematoporphyrin, and the like by the procedures described by Mew, D. et al, *J.Immunol.* 130:1473-1477 (1983) and Mew, D. et al, *Cancer Res.* 45:4380-4386 (1985), the entire contents of which and the publications cited therein being hereby incorporated by reference in their entireties.

The reagents of this invention can be used in immunohistopathology examinations of tissues obtained by biopsy or surgery, for example. to identify adenocarcinoma cells. Samples of tissue removed during surgery or biopsy are prepared and mounted on slides by standard procedures such as those described by Koss, L. DIAGNOSTIC CYTOLOGY AND ITS HISTOPATHOLOGIC BASIS. Philadelphia:Lippincott (1979), and Luna, L., MANUAL OF HISTOLOGIC STAINING METHOD OF THE ARMED FORCES INSTITUTE OF PATHOLOGY. 3rd ed. New York:McGraw-Hill (1968), and Borowitz, M. et al, *The Journal of Histochemistry and Cytochemistry.* 30:171-174 (1982). In general, the tissue is quick frozen and frozen sections are prepared and mounted on slides.

In these staining procedures, the ADCA binding antibody is applied to the sample being tested. The ADCA binding antibody can be applied to a tissue section on the slide in an aqueous solution. The solution preferably contains suitable salts and buffers to preserve the reactants and facilitate the binding reaction. For example, the solution can contain protein such as bovine serum albumin (BSA), phosphate buffer solution (PBS), and a mild surfactant. The rinse solution described below can also be used.

The buffered solution can contain from 1 to 100 μg/mL and preferably contains from 10 to 25 μg/mL of the primary antibody in an aqueous phosphate buffered solution having a phosphate molarity of from 0.005 to 0.1 and a pH of from 6.0 to 8.0. A phosphate molarity of from 0.01 to 0.5, and a pH of from 7.2 to 7.6 are preferred. The primary antibody solution is maintained in contact with the cell smear until binding with antigen can occur. The incubation time is temperature dependent. At temperatures of from 18° to 40° C., incubation times of from 30 to 180 minutes can be used. At room temperature, incubations times can be from 1 to 60 minutes and preferably from 5 to 30 minutes. The excess primary antibody solution is then removed, and the slide is rinsed with a suitable rinse solution. Rinse solutions can be aqueous phosphate buffered solutions having a phosphate molarity of from 0.1 to 0.5, a pH of from 6 to 8.

In one preferred method of this invention, a biotin labeled primary antibody (ADCA binding antibody) is applied, and following the first step, the primary antibody is bound to the respective antigens present in the sample.

In the preferred embodiment of this invention, the tissue section is then contacted with an avidin-(labeled biotin) complex. If a secondary antibody is labeled with biotin, the preferred avidin-biotin complex is prepared by mixing a large molar excess of avidin with the biotinylated enzyme. Biotin and avidin can be optionally interchanged or mutually substituted- in the method and reagents of this invention, in which instance, corresponding adjustments in molar ratios between biotin and avidin derivatives are required.

The avidin or biotin can be labeled with any conventional label such as a luminescent substance such as a phosphor or fluorogen, a bioluminescent substance, a chemiluminescent substance, a radioactive substance, an enzyme, chromophor, pigment, spin label, or metal containing substance. These labels are covalently bonded to the avidin or biotin by conventional procedures appropriate to the chemical groups on the label. Procedures for covalently bonding radioactive isotopes, fluorophors and enzymes to avidin or biotin can be the same procedures described above for binding the respective labels to ADCA binding antibodies, for example.

The avidin-biotin complex is applied to the tissue section in a suitable aqueous buffer solution such as the PBS solutions described above for applying antibodies to the cell smear. The complex solution is applied to the tissue section for a time sufficient to permit binding of the avidin-biotin complex with the avidin or biotin which is covalently bonded to the secondary antibody, if any. Following this step, the excess avidin-biotin complex solution is removed, and the tissue section is preferably rinsed with a suitable rinse solution such as the rinse solution described above, for example.

The slide is then examined by procedures appropriate for the particular avidin-biotin complex label employed. These procedures are conventional. For example, if a radioactive label is employed, the slide can be examined with a Geiger counter to measure the level of residual radioactivity on the slide. Alternatively, if the label is a phosphor or a fluorogen, it can be examined under a fluorescent microscope. If the label is a chromophor or a pigment, the slide can be examined under a microscope using ordinary light. The cells to which ADCA binding antibody is significantly bound (only malignant cells) are labeled, showing they are malignant.

In the preferred embodiment of this invention, the biotin-avidin complex has an enzyme label. Suitable enzymes and substrate systems are described in U.S. Pat. Nos. 4,190,496 and 4,208,479, and in Hawk, et al, PRACTICAL PHYSIOLOGICAL CHEMISTRY. New York:McGraw-Hill pp 306-307 (1954), which are hereby incorporated by reference. The system selected is designed to provide the distinguishing characteristics desired. Preferred systems employ oxidoreductases such as horseradish peroxidase and a substrate such as diaminobenzidine. The horseradish peroxidase and diaminobenzidine provide a pronounced pigmentation or stain of the malignant cell which contrasts strongly with available counter-stains. Any other enzyme-substrate combinations providing a basis for clearly distinguishing the malignant and normal cells can be used.

In an alternative method, the primary antibody is a ADCA binding non-human antibody and is unlabeled. Following the initial step, the primary antibody is bound to the respective target antigens present in the sample. In the following steps, the bound antibody is coupled with successive multiplying reagents to obtain amplification and increase sensitivity of the procedure. In a next step, a biotin labeled secondary antibody which binds selectively with the class of antibodies from which the primary antibody is selected is applied to the sample. This secondary antibody is applied to the tissue section in a suitable aqueous solution for a time sufficient to permit binding between the secondary antibody and any primary antibody bound to cell antigens. In general, the secondary antibody is preferably a monoclonal antibody which binds to the class of immunoglobulin to which the primary antibody is a member, for example to the Fc portion of the primary antibody. For primary antibodies of the IgM, $IgG_1$, $IgG_{2a}$, $IgG_{2b}$, IgA, and other classes, for example, secondary antibodies binding to the respective Fc portions or the primary antibodies are selected.

The biotin is covalently bonded to the secondary antibody by conventional procedures such as those described above for binding biotin to the primary antibody with a large molar excess of biotin to antibody, preferably with a molar ratio of at least 100:1 biotin to antibody. The biotin labeled secondary antibody is applied to the tissue section in an aqueous solution which is preferably the phosphate buffered solution described above as the vehicle for the original primary antibody. The solution is contacted or incubated with the cells on the slide for a time sufficient to permit binding between the primary antibody and the primary antibody, if any is present, to occur. The preferred incubation times and temperatures correspond to those described above with respect to the treatment of the smears with the primary antibody solution in the first step. Following incubation, the excess secondary antibody solution is removed, and the slide is rinsed with a suitable rinse solution. The rinse solution described above is preferred.

The reagents of this invention can be used in sandwich and competition immunoassays to detect substances having the ADCA antigen epitope in the blood or other body fluid, the presence of the substances in the fluid being indicative of adenocarcinoma.

A competition immunoassay embodiment of this invention is a method for determining the presence and amount of ADCA antigen in a body fluid, for example blood plasma. In the method, the sample is mixed with a predetermined amount of labeled ADCA antigen or labeled ADCA antiidiotype antibody, and the mixture is contacted with an insoluble support to which ADCA binding antibody is adhered. The amount of ADCA binding antibody is insufficient to bind all of the sample analyte and the labeled ADCA antigen or ADCA antiidiotype antibody. The mixture is contacted with the insoluble support for a time sufficient to permit antigen-antibody binding to occur, and the sample is removed from the support. The label bound remaining on the insoluble support is then measured. The label can be a physically detectable label which can be measured directly on the insoluble support. Alternatively, the label can be a moiety which upon subsequent treatment yields a physically detectable label. For example, if the label is an enzyme label, the insoluble support can be contacted with a substrate for the enzyme which will yield a measurable fluorophore or chromophore. The amount of label measured is an inverse function of the amount of the ADCA antigen in the body fluid.

A sandwich immunoassay embodiment of this invention is a method for determining the presence and amount of ADCA binding antibody in a body fluid sample, for example blood plasma. In this method, the body fluid is contacted with an insoluble support to which ADCA antigen or ADCA antiidiotype antibody is adhered for a time sufficient to permit antigen-antibody binding to occur, and the sample is removed from the support. The insoluble support is then contacted with an anti-Ig antibody (i.e., secondary antibody) to bind with any sample antibody bound to the insoluble support. The presence of secondary antibody on the insoluble support is then determined. The secondary antibody can have a physically detectable label which can be measured directly on the insoluble support. Alternatively, the secondary antibody can be unlabeled, and the secondary antibody can be determined by contacting the insoluble support with a labeled antibody which binds selectively with the secondary antibody (i.e., a tertiary antibody), removing unbound labeled tertiary antibody from the support, and determining the presence of the label on the insoluble support.

The antibody and antigen reagents can be bonded to an insoluble support by conventional processes. Procedures for binding of antibodies to insoluble supports are described in U.S. Pat. Nos. 3,551,555, 3,553,310, 4,048,298 and RE-29,474, and by Tijssen, P. LABORATORY TECHNIQUES IN BIOCHEMISTRY AND MOLECULAR BIOLOGY: PRACTICE AND THEORIES OF ENZYME IMMUNOASSAYS. New York: Elsevier (1985), for example. Procedures for binding of antibodies to polystyrene by adsorption are described in U.S. Pat. Nos. 3,646,346 and 4,092,408, for example. These same procedures are suitable for binding proteinaceous antigens to insoluble supports.

A variety of materials can be used as the insoluble support, the primary consideration being the binding of the antibody or antigen to the surface, the absence of interference with the reagent binding reaction or with other reactions which can be employed to determine the presence and extent of the binding reaction. Organic and inorganic polymers, both natural and synthetic, can be used as the insoluble support. Examples of suitable polymers include polyethylene, polypropylene, polybutylene, poly(4-methylbutylene), butyl rubber, silastic polymers, polyesters, polyamides, cellulose and cellulose derivatives (such as cellulose acetate, nitrocellulose and the like), acrylates, methacrylates, vinyl polymers (such as polyvinyl acetate, polyvinyl chloride, polyvinylidene chloride, polyvinyl fluoride, and the like), polystyrene and styrene graft copolymers, rayon, nylon, polyvinylbutyrate, polyformaldehyde, etc. Other materials which can be used as the insoluble support are the latexes of the above polymers, silica gel, silicon wafers, glass, paper, insoluble protein, metals, metalloids, metal oxides, magnetic materials, semi-conductive materials, cermets and the like. In addition are included substances which form gels, e.g. proteins such as gelatins, lipopolysaccharides, silicates, agarose, polyacrylamides or polymers which form several aqueous phases such as dextrans, polyalkylene glycols (alkylene with 2 to 3 carbon atoms) or surfactants, e.g. amphophilic compounds such as phospholipids, long chain (12-24 carbon atoms) alkyl ammonium salts, and the like.

The preferred support comprises a nylon or nitrocellulose membrane. An alternate diagnostic support is made from polystyrene, styrene copolymers such as styrene-acrylonitrile copolymers, or polyolefins such as polyethylene or polypropylene, and acrylate and methacrylate polymers and copolymers. The antibody and antigen reagents can be bound to the insoluble support by adsorption, ionic bonding, van der Waals adsorption, electrostatic bonding, or other non-covalent bonding, or it can be bound to the insoluble support by covalent bonding. A particularly advantageous support for this procedure comprises a microtiter plate having a plurality of wells. The well surface or plastic cup inserts therein can constitute the antigen or antibody support. If the determination will require the use of fluorometric measurements, the microtiter plate or the well inserts are advantageously opaque to light so that excitation light applied to a well does not reach or influence contents of the surrounding wells.

Procedures for non-covalent bonding are described in U.S. Pat. No. 4,528,267. Procedures for covalently bonding antibodies and antigens to insoluble supports are described by Ichiro Chibata in IMMOBILIZED ENZYMES. Halsted Press: New York (1978) and A. Cuatrecasas, J.Bio.Chem. 245:3059 (1970), the entire contents of which are hereby incorporated by reference. The surface can be coated with a protein and coupled with the antibody or antigen using procedures described in U.S. Pat. No. 4,210,418 using glutaraldehyde as a coupling agent, for example. In a still further procedure, the well can be coated with a layer having free isocyanate groups such as a polyether isocyanate, and application of the antibody or antigen in aqueous solution thereto effects the requisite bonding. In a still further procedure, the antibody or antigen can be coupled to a hydroxylated material by means of cyanogen bromide as described in U.S. Pat. No. 3,720,760.

The insoluble supports are preferably "blocked" to reduce nonspecific binding. The choice of suitable blocking agents is determined by the type of insoluble support. For example, for polystyrene supports, suitable blocking agents include water-soluble non-immune animal proteins and polyamino acids. Suitable water-soluble non-immune animal proteins include albumins such as bovine (BSA), human, rabbit, goat, sheep, and horse serum albumins; and other animal proteins such as fetal calf serum, ovalbumin, fibrinogen, thrombin, transferrin, glycoproteins, and the like. Suitable water-soluble polyamino acids include polymers of one or more amino acids such as lysine, glutamic acid, alanine, histidine, methionine, proline, and the like.

The same blocking agents can also be used for nylon and nitrocellulose supports. However, a preferred blocking agent for nitrocellulose or nylon membrane supports is non-fat milk or casein. An optimum blocking agent for these membrane supports is an aqueous solution containing 5 wt. % non-fat dried milk and nonionic surfactants such as polyoxyethylene sorbitan derivatives and polyoxyethylene ethers.

Methods for tumor localization and therapy with labeled antibodies specific for adenocarcinoma can be carried out as described in U.S. Pat. Nos. 4,460,561, the entire contents of which are hereby incorporated by reference.

The diagnostic media for administration is formed using physiologically acceptable media in a manner fully within the skill of the art. For example, the radio-labeled ADCA binding antibody or binding fragment thereof, preferably MS2B6 hMAb, optionally with the addition of pharmaceutically acceptable excipients, are suspended or dissolved in an aqueous medium, and then the solution or suspension is sterilized. Suitable additives include non-immune proteins, and other stabilizing, pharmaceutically acceptable, non-toxic additives. Intravenous solutions must be sterile, free from physiologically unacceptable agents, and should be isotonic or iso-osmotic to minimize irritation or other adverse effects upon administration. Suitable vehicles are aqueous vehicles customarily used for administering parenteral solutions such as Sodium Chloride Injection, Ringer's Injection, Dextrose Injection, Dextrose and Sodium Chloride Injection, Lactated Ringer's Injection, and other solutions such as are described in REMINGTON'S PHARMACEUTICAL SCIENCES. 15the Ed., Easton: Mack Publishing Co. pp 1405-1412 and 1461-1487 (1975) and THE NATIONAL FORMULARY XIV. 14th Ed. Washington: American Pharmaceutical Association (1975), the contents of which are hereby incorporated by reference. The solutions can contain preservatives, antimicrobial agents, buffers and antioxidants conventionally used in parenteral solutions, selecting excipients and other additives which are compatible with the antibodies and which will not interfere with the manufacture, storage or use of the products.

The radio-labeled antibodies of this invention are administered to patients for imaging in amounts which are sufficient to yield the desired image. Generally, dosages of from 0.01 to 0.1 mCi of imaging agent per kilogram of patient body weight are effective to obtain an image of most organs.

Methods for applying the radiochemical agents for imaging, and the equipment and methods for imaging are described by Alazraki, N., et al, FUNDAMENTALS OF NUCLEAR MEDICINE. New York: The Society of Nuclear Medicine, Inc. (1984); THE CHEMISTRY OF RADIOPHARMACEUTICALS. Heindel, N. et al, Editors, Chicago: Masson Publishing (1978); and RADIOPHARMACEUTICALS: PROGRESS AND CLINICAL PERSPECTIVES. Fritzberg, A. Editor, Boca Raton: CRC Press (1986), and the publications cited therein, the entire contents of each of these publications and the reference citations included therein being hereby incorporated by reference in their entireties.

For radiotherapy, the dosage and radioactive agent concentration are selected to provide effective therapeutic results, and must be adjusted to the location and type of tumor, the patient, and the total therapeutic regimen being administered. Generally, dosages of 50 to 150 mCi of agent can be used. The injection can be intravenous, intraarterial, intraperitoneal or intrathecal. Intradermal and intracavitary administration are advantageous for tumors restricted to areas close to regions of the skin and/or particular body cavities. The compositions for radiotherapy can be the same as listed above for radioimaging.

For immunotoxin therapy, the immunotoxins are administered to in solutions the patient in therapeutically effective amounts (i.e., amounts that eliminate or reduce or retard the increase of the patient's tumor burden). They will normally be administered parenterally, preferably intraperitoneally. The dose and dosage regimen must be selected to correspond to the nature of the cancer (primary or metastatic) and its population, the characteristics of the immunotoxin, e.g., its therapeutic index, the patient, and the patient's history. The amount of immunotoxin administered (IP) will typically be in the range of from about 0.01 to about 100 mg/kg and preferably from 0.01 to 10 mg/kg of patient weight.

ADCA antigen is an antigen of epithelial differentiation which is expressed by some fetal tissues and persists in adult epithelia of the fallopian tube, endometrium endocervix, colon, bronchus, breast, sweat duct and large renal ducts. It is notably absent from peritoneal mesothelial cells, blood-borne cells or tissue stroma cells. The ADCA antigen is expressed by epithelial ovarian cancer cells, as well as a large proportion of nonovarian adenocarcinomas, but has not been found to be associated with squamous call cancer, sarcoma, melanoma, lymphoma or malignant germ cell tumors. The target epitope ADCA resides on polypeptides of 38, 44 and 60 kD, and probably does not involve sialic acid residues or glycolipid structures. The binding of MS2B6 IgM to viable ovarian cancer cells, the protease-sensitive nature of such binding, and the distribution of the antigen as revealed by immunoperoxidase studies, suggest that a significant portion of the ADCA antigen is located on the cell surface. At least in the patient of origin, the existence of the human MAb MS2B6 IgM establishes that its target antigen can be immunogenic in humans.

This invention is further illustrated by the following specific but non-limiting examples. Temperatures are given in degrees Centigrade and percentages as weight percents unless otherwise specified. Procedures which have been previously carried out are presented in the past tense, and procedures which are being constructively reduced to practice in this application are presented in the present tense.

EXAMPLE 1

MS2B6 IgM Antibody

Human hybridoma MS2B6 (American Type Culture Collection deposit ATCC HB 9765) is grown in serum-free medium (Iscoves with 1% Nutridoma-NS, Boehringer-Mannheim) and produced IgM at a rate of 32 µg per $10^6$ cells per day. Supernatant fluids containing approximately 60 µg/mL IgM were concentrated 100-fold by ultrafiltration using a membrane with 300,000 dalton molecular weight cut-off (Amicon). The MS2B6 IgM was purified by HPIEC using a Model 1084B liquid chromatograph (Hewlett Packard) and a 0.75×7.5 cm TSK-DEAE-5PW column (Bio Rad). Buffer A consisted of 0.02M Tris, 0.1M sodium chloride, pH 8.5. Buffer B consisted of 0.02M Tris, 0.6M sodium chloride, pH 7.0. The column was equilibrated with 10 (v/v)% Buffer B in Buffer A, and the samples were applied. The column was eluted with 25 (v/v)% Buffer B in Buffer A. The eluted IgM was concentrated and stored frozen in liquid nitrogen. The purity of the final product was approximately 95% IgM by SDS-PAGE.

EXAMPLE 2

Biotin Labeled MS2B6 IgM Antibody

Biotin labeling was effected by the method of Haspel, M. et al, Cancer Res. 45:3951-3961 (1985) with modifications. The HPIEC-purified produce of Example 1 at 1 mg/mL was dialyzed against 0.01M potassium phosphate and 0.15M potassium chloride, pH 7.8. Biotin: N-hydroxysuccinimide (Sigma) dissolved at 1 mg/mL in DMSO was added to give a molar ratio of biotin to IgM of 30:1 (using the molecular weight of monomer IgM of 180,000). After 15 min at room temperature with agitation, one-tenth volume of 1M ammonium chloride was added, and the solution was dialyzed against PBS with 0.02 % sodium azide.

EXAMPLE 3

$^{125}$I-Labeled MS2B6 IgM Antibody $^{125}$I-labeling was achieved using the Bolton-Hunter reagent (Bolton, A. et al, Biochem.J.133:529-1083 (1974)). 250 µCi of the reagent (Amersham) was evaporated, and the HPIEC-purified product of Example 1, dialyzed against 0.1M sodium borate buffer, pH 8.5, was added. After 20 min at $0°$ C., 0.5 mL of 0.2M glycine in borate buffer was added to stop the reaction. Unincorporated $^{125}$I was separated from $^{125}$I-labeled MS2B6 IgM by exclusion chromatography on Sephadex G-25 (Pharmacia). Specific activities in the range of 1 to 5 µCi per µg were obtained.

EXAMPLE 4

Radio-iodine Labeled MS2B6 IgM Antibody

Repeating the procedure of Example 3 but replacing the $^{125}$I reagent with the corresponding hu 123I and $^{131}$I reagents yields the corresponding $^{123}$I-labeled MS2B6 IgM and 131I-labeled MS2B6 IgM.

EXAMPLE 5

Radio-metal Labeled MS2B6 IgM Antibody

In this procedure the antibodies are conjugated with a chelating agent such as diethylenetriaminepentaacetic acid which is capable of forming a chelate with the metallic radionuclide. A suspension of 0.1 mg/mL of the bicyclic anhydride of DTPA (diethylenetriaminepentaacetic acid) is prepared in a dry solvent such as chloroform, ether or dry DMSO. An aliquot is removed to a clean, dry tube sufficient to provide a DTPA to immunoglobulin molar ratio of 1:1 and evaporated under nitrogen. A 10-20 microliter portion of the antibody solution used (10-20 mg/mL) in 0.05M bicarbonate buffer in saline, pH 7.0-7.5 is added to the dry DTPA, and the contents are agitated for 0.5-1.0 min. The coupled protein preparation is diluted to 0.2 mL with the same buffer solution and purified on a 5 cm gel filtration column with SEPHADEX G-50 gel, using a saline eluant. The coupling efficiency is determined before purification by the addition of "chelation-grade" $^{111}$In in 0.5M acetate buffer solution, pH 6.0. Thin layer chromatography is used to separate the DTPA coupled antibody for calculation of the coupling efficiency. The DTPA-coupled antibodies are stored at 4° C. until needed for binding with metallic radionuclides such as $^{111}In^{+3}$, $^{212}Bi^{+3}$, $^{99m}Tc$, and $^{68}Ga^{+3}$ to form the corresponding chelates.

EXAMPLE 6

Immunoperoxidase Studies

Procurement of human tissues had the approval of the Human Subjects Committee at Stanford University and was obtained after surgery or autopsy through the Department of Surgical Pathology. Pathology reports on each malignant tissue were reviewed. The fresh tissues were cut into small pieces, wrapped in foil and stored in liquid nitrogen until immediately prior to transfer to embedding medium. Six micron cryostat sections were air dried and stored at 4° C., then fixed immediately prior to use with PLP fixative using the procedure of McLean, I. et al, *J.Histochem.Cytochem.* 22:1077–1083 (1974a) (0.5% paraformaldehyde, 0.075M L-lysine, and 0.01M sodium periodate). The sections were fixed for 10 min at 4° C. followed by washing in PBS. Some tissues required blocking of endogenous biotin following the procedure of Wood, G. et al. *J.Histochem.Cytochem.* 29:1196–1204 (1981). Suppression of endogenous peroxidase activity was effected by the procedure of Kelley, J. et al, *J.Immunol.Meth.* 96:127–132 (1987). Immunoperoxidase staining with biotin-labeled MS2B6 IgM or control IgM was performed in the manner of Hancock, W. et al, *Meth.Enzymol.* 121:828–848 (1986), briefly as follows. The sections were sequentially incubated (with PBS washing between) with 10% fetal calf serum to block, biotin-labeled antibody at 30 μg/mL, streptavidin-HRP (Sigma) at 0.5 μg/mL, then diaminobenzidine (Sigma) at 1 mg/mL with 0.03% hydrogen peroxide. After 15 min. slides were washed with water, counterstained with hematoxalin and coverslipped. Microscopically, positive staining by biotin-labeled MS2B6 IgM was visualized as deposition of brown stain on cells not stained by biotin-labeled control IgM.

Fixation of the sections with paraformaldehyde-lysine-periodate allowed adequate tissue preservation as well as antigen staining. gluteraldehyde (0.1%) and neutral formalin (2%) preserved some antigen staining, but methanol fixation was not effective, destroying antigen staining.

Forty-one different ovarian epithelial cancer tissues were stained for biotin-labeled MS2B6 IgM binding and the results shown in Table C.

TABLE C

MS2B6 IgM Immunoperoxidase Studies
Epithelial Ovarian Cancer

| Subtype | Borderline | Tumor Grade I | II | III | Total |
|---|---|---|---|---|---|
| Papillary Serous | 2/2* | — | 10/10 | 18/18 | 30/30 |
| Mucinous | 1/1 | 1/1 | — | 2/2 | 4/4 |
| Endometrioid | — | 1/1 | 3/3 | 2/2 | 6/6 |
| Clear Cell | — | — | — | 1/1 | 1/1 |
|  |  |  |  |  | 41/41 |

*Number of cases positive divided by number tested

As shown in Table C, 41 of 41 specimens stained positively, including 30 serous papillary, 4 mucinous, 6 endometrioid and 1 clear cell tumor. The single example of a borderline mucinous tumor from a patient with psuedomyxoma peritonii demonstrated marked hertergeneity of expression of target antigen with weak, patching staining. Heterogeneous expression of the antigen was absent or minimal in the other tissues examined, which showed remarkable uniformity in staining. The staining pattern was almost always a ring-like or lattice distribution around cell peripheries, except for one example of a high grade mucinous carcinoma in which the antigen was clearly distributed throughout the cytoplasm. Among the serous carcinomas, positive staining was independent of tumor grade.

Forty-five different nonovarian and nonepithelial ovarian malignant tissues were examined for ADCA antigen staining, and the results are shown in Table D.

TABLE D

MS2B6 IgM Immunoperoxidase Studies
Other Cancers

| Tumor Type | Origin | MS2B6 Staining* |
|---|---|---|
| Squamous Cell Carcinoma | Cervix | 0/4 |
| Squamous Cell Carcinoma | Vulva | 0/3 |
| Squamous Cell Carcinoma | Ovarian Teratoma | 0/1 |
| Adenocarcinoma | Cervix | 1/1 |
| Adenocarcinoma | Endometrium | 5/10 |
| Adenocarcinoma | Breast | 2/2 |
| Adenocarcinoma | Lung | 1/1 |
| Adenocarcinoma | Colon | 5/5 |
| Adenocarcinoma | Pancreas | 1/1 |
| Adenocarcinoma | Ovarian Krukenberg | 1/1 |
| Undifferentiated Carcinoma | Pelvis (unknown primary) | 1/3 |
| Mesothelioma | Peritoneum | 1/1 |
| Transitional Cell Carcinoma | Kidney | 1/1 |
| Leiomyosarcoma | Uterus | 0/1 |
| Malignant Mixed Mullerian Tumor | Uterus | 0/2 |
| Malignant Mixed Mullerian Tumor | Ovary | 0/1 |
| Adenocarcinoma | Uterus | 0/1 |
| Immature Teratoma | Ovary | 1/1 |
| Endodermal Sinus Tumor | Ovary | 0/1 |
| Dysgerminoma | Ovary | 0/1 |
| Melanoma | Peritoneal Cavity | 0/2 |
| Lymphoma | Omentum | 0/1 |

*Number positive divided by number tested

Eight examples of squamous cell carcinoma, 5 sarcomas and 2 of 3 ovarian germ cell cancers were negative for ADCA antigen expression. One ovarian immature teratome did have positive staining, but only in areas of mature, benign epithelium. The majority of 20 nonovarian adenocarcinomas stained positively for ADCA antigen including 5 of 10 endometrial adenocarcinomas and 5 of 5 colon adenocarcinomas. In addition, 1 of 3 undifferentiated carcinomas (unknown primary), a mespthelioma (peritoneum) and a transitional cell carcinoma (kidney) stained positively. Examples of malignant melanoma and lymphoma were negative.

Seventy-three different normal adult and fetal tissue specimens were examined for ADCA antigen staining, and the results are shown in Table E.

TABLE E

MS2B6 IgM Immunoperoxidase Studies
Normal Human Tissues

| Tissue Type | MS2B6 Staining* | Staining Characteristics |
|---|---|---|
| Ovary | 0/5 |  |
| Fallopian Tube | 4/4 | Epithelium only |
| Myometrium | 0/4 |  |
| Endometrium | 3/4 | Epithelium only |
| Endocervix | 2/2 | Epithelium only |
| Vagina | 0/1 |  |
| Peritoneum | 0/3 |  |
| Bladder | 1/1 | Epithelium only |
| Kidney | 3/4 | Large tubular epithelium only |
| Prostate | 2/2 | Epithelium only |
| Salivary Gland | 1/1 | Epithelium only |
| Esophagus | 0/1 |  |
| Stomach | 0/1 |  |

TABLE E-continued

MS2B6 IgM Immunoperoxidase Studies
Normal Human Tissues

| Tissue Type | MS2B6 Staining* | Staining Characteristics |
|---|---|---|
| Small Bowel | 1/1 | Weak staining, epithelium only |
| Gall Bladder | 0/1 | |
| Colon | 4/4 | Epithelium only |
| Liver | 1/4 | One specimen, weak staining |
| Lung | 3/3 | Bronchiolar epithelium only |
| Breast | 3/3 | Ductal epithelium |
| Skin | 1/1 | Sweat duct epithelium only |
| Spleen | 0/2 | |
| Thymus | 0/1 | |
| Brain | 0/2 | |
| Thyroid | 1/2 | One specimen, very weak patchy staining |
| Placenta, midtrimester | 1/2 | Syncytiotrophoblast epithelium |
| Placenta, term | 1/1 | Syncytiotrophoblast epithelium patchy staining |
| Fetal Intestine | 1/1 | |
| Fetal Liver | 6/7 | |
| Fetal Skin | 0/2 | |
| Fetal Kidney | 1/2 | One specimen, weak staining |
| Fetal Bladder | 1/1 | |

*Number positive divided by number tested

Positive staining was found among certain normal nonsquamous epithelia including fallopian tube, endocervix, endometrium, bronchus, colon, mammary ducts, large renal ducts, salivary glands, sweat ducts and bladder. Weak patchy staining was noted in single examples of liver, thyroid and small bowel epithelium. The strongest and most uniform staining was of fallopian tube, endometrial and bronchial epithelia.

Several tissues, including kidney, liver and colon demonstrated significant staining of epithelia when the biotin-labeled negative control IgM preparation was used to stain the tissues. In the case of liver, the vast majority of this background binding was removed by blocking for endogenous biotin activity. Even after blocking of endogenous biotin, several specimens of colon epithelium demonstrated significant binding of negative control biotin-labeled IgM, though binding of biotin-labeled MS2B6 IgM was always more intense. Most, but not all, of this background control IgM staining of colon epithelium could be removed by blocking for endogenous peroxidase. As similar phenomenon was observed for several specimens of kidney epithelium. Here MS2B6 IgM staining was weak and generally confined to the epithelium of large ducts, glomeruli being totally negative. Control IgM staining of kidney resulted in a similar but even less intense pattern, even after blocking of endogenous biotin.

The absence of the ADCA antigen from the peritoneal and ovarian epithelial was of interest. In addition, the antigen was not detected among epidermoid epithelia, except in the sweat gland ducts in the skin. Among fetal tissues, the antigen was intensely expressed in examples of syncytiotrophoblast epithelium as well as in fetal intestinal, hepatic and renal epithelia. Six specimens of benign lesions were tested for ADCA antigen including 2 benign ovarian cysts, 2 uterine leiomyomata, 1 ovarian fibroma and 1 hydatidiform mole. These did not show staining.

In addition to the absence of MS2B6 IgM staining of normal spleen and thymus, other lymphoid collections such as those located in intestinal submucosa were negative for staining. Among all tissues examined, intravascular elements were always negative for MS2B6 IgM staining.

To independently test for MS2B6 IgM binding to elements of the blood (e.g., RBC, lymphocytes, granulocytes, platelets), further testing was performed. MS2B6 IgM at 50 µg/mL was tested by the Stanford Transfusion Service using standard hemoagglutination techniques. MS2B6 IgM failed to react with a panel of red blood cells expressing the following antigens: Blood group antigens A and B, Rh antigens D, C, c, E and e; Kell antigens K, k, $K^b{}_p$ and $J^b{}_s$; Duffy antigens $F^s{}_y$ and $F^b{}_y$; Kidd antigens $J^a{}_k$ and $J^b{}_k$; Lewis antigens $Le^a$ and $Le^b$; MN antigens M, N, S and s; and Lutheran antigens $Lu^a$ and $Lu^b$; and $X^a{}_g$ antigen.

MS2B6 IgM at (50 µg/mL) was also tested by the Stanford Blood Bank for granulocyte agglutination and for cytotoxicity to granulocytes, lymphocytes and platelets based on a carboxylfluoroscein diacetate uptake procedure described by Lizak, G. et al, Human Immunol. 8:265-272 (1983). Four different granulocyte specimens were negative for MS2B6 IgM induced aggregation or cytotoxicity. Four different lymphocyte specimens and 6 different platelet preparations showed no MS2B6 IgM induced cytotoxicity.

EXAMPLE 7

Electrophoresis and Immunoblotting

SDS-PAGE was performed using the discontinuous buffer system of Laemmli, U. Nature (London) 227:680-685 (1970), with 4% stacking and 10% running gels. Samples consisted of purified ovarian cancer ascites tumor cells or ovarian cancer cell line 2774. Preparation of the ascites tumor cells is described below. The ovarian cancer cell line 2774 was grown to confluence in Dulbecco's Modified Eagles Medium with 10% fetal calf serum, scraped off the flasks, and washed in PBS. SDS sample buffer containing 2-mercaptoethanol was added (100 µl per 10⁶ cells), and the samples heated to 100° C for 3 min. Human IgM (200 ng) was run in control lanes to confirm transfer after immunoblotting.

Blotting onto nitrocellulose paper was effected as described by Towbin et al, Proc.Natl.Acad.Sci. (U.S.A.) 76:4350-4354 (1979). The blots were blocked by incubation in 4% nonfat milk with PBS for 1 hr at room temperature. Indirect immunostaining was performed by the alkaline phosphatase method of O'Connor, et al, J.Immunol.Meth. 54:267-271 (1982) as modified by Sidberry et al, J.Immunol.Meth. 76:299-305 (1985). Unlabeled MS2B6 IgM or control IgM (human serum IgM, Cepel) was incubated with the blot at 5 to 10 µ/mL for 4 hr followed by PBS washing. Next, the blots were incubated with alkaline phosphatase-labeled goat anti-human IgM (1:100, Sigma) for 2 hr, PBS washed, then placed in 50 mM Tris, pH 8.3. Freshly prepared chromagen solution (Naphtol AS-MX phosphate, 1 mg/ml; Fast Red TR salt, 2 mg/mL; both from Sigma, in 50 mM Tris, pH 8.3) was added and incubation continued until color development reached the desired level. The blots were then washed with water and air dried.

Radioimmunoblotting was performed in an analogous way. After blocking, $6 \times 10^6$ labeled MS2B6 IgM was added, and incubation was continued for 4 hr at room temperature. After washing with PBS, the blots were air dried and autoradiographed using Kodak AR film.

Immunoblot analysis of whole cell extracts of both purified ascites cells and ovarian cancer cell line 2774 consistently revealed several MS2B6 IgM staining bands not observed in blots stained with negative control IgM (human serum IgM). The major components consisted of bands of 38 kD, 44 kD and 60 kD Although some heterogeneity was apparent, the 38 kD species was the prominent band among ascites tumor cell preparations. None of these bands appeared after staining identical blots for control IgM binding. The lower molecular weight bands appearing in the control IgM blot were also faintly present in the MS2B6 blots, the difference in intensity most likely being due to a deliberately longer development time for the control IgM blot.

Radioiodinated MS2B6 IgM was used in blotting experiments to confirm antigenic recognition prior to use in the biodistribution studies described in Example 10. The $^{125}$I-labeled MS2B6 IgM radioimmunoblotting of a whole cell extract of purified ovarian cancer ascites tumor cells resulted in identification mainly of the 38 kD band, although in other experiments, the 44 kD band also accumulated some label. No bands were identified after incubation of similar blots with $^{125}$I-labeled control IgM.

EXAMPLE 8

Immunofiltration

Ovarian cancer ascites tumor cells were prepared as described by Smith, L. et al. *J.Immuno.Meth.* 105:263-273 (1987). Tumor cell suspensions of 90 to 95% purity resulted after removal of contaminating red blood cells, lymphocytes and macrophages by treatment of crude cell suspensions with carbonyl iron followed by buoyant centrifugation in 36% PERCOL (Pharmacia). A pool of 4 different ovarian cancer ascites tumor cell preparations was used. The cells were washed in PBS, and the pelleted cells suspended in solutions of enzymes or fixatives as follows: (i) PBS (with calcium and magnesium); (ii) Trypsin, 500 μg/mL in PBS; (iii) Pronase, 500 μg/mL in PBS; (iv) Neuraminidase (Gibco), 10 U/mL in PBS; (v) PLP fixative using the procedure of McLean, I. et al (supra), 0.5% paraformaldehyde, 0.075M L-lysine, and 0.01M sodium periodate; (vi) Gluteraldehyde, 0.1 % in PBS; (vii) Formaldehyde, 4% in PBS; (viii) Methanol, 100%; and (ix) Ethanol, 100%. Enzyme suspensions were incubated at 37° C. for 10 min. Fixative suspensions were incubated at room temperature for 10 min.

Aliquots of the treated cells (2 × 10$^5$ cells/well) were placed into wells of an immunofiltration device (Biorad) assembled with a fiberglass filter. The cells were washed with PBS and stained with MS2B6 IgM. 0.1 mL aliquots of MS2B6 IgM (25 μg/mL in PBS) were allowed to run through the wells, followed by 0.1 mL biotin-labeled goat anti-human IgM (1:1000, Sigma), 0.1 mL streptavidin-peroxidase (0.5 μg/mL, Sigma), and chlornaphthol-hydrogen peroxide solution, with PBS washings between each solution. After color development was complete, the wells were washed with water, and the fiberglass filter dried.

Treatment of ascites tumor cells with two proteases resulted in substantial reduction in staining, while neuraminidase under conditions which are known to remove sialic acid residues from sheep RBC, did not affect binding. In other experiments not described here, MS2B6 IgM binding was unaffected by treatment of ascites cells with phospholipases A$_2$, C and D or by chitinase.

We also attempted to identify any glycolipid structures which might bind MS2B6 IgM by immunostaining thin layer chromatographic separations of lipid extracts of ascites tumor cells using methods similar to those described by Magnani et al. *J.Biol.Chem.* 257:14365-14369 (1982). No glycolipid binding was found.

Gluteraldehyde fixation retained more activity than did formalin. Methanol treatment almost completely abolished antigenic activity, and ethanol caused substantial reduction.

EXAMPLE 9

CA125 Immunoassay

An enzyme-linked immunoassay for ovarian cancer-associated antigen Ca125 was performed according to the insert in the test kit (Ca125 test kit, Abbot). To 100 μL of Ca125 standard (168 U/mL) were added aliquots of OC125 or MS2B6 IgM. After subsequent incubation with OC125-beads and OC125-peroxidase conjugate, the beads were washed, developed and optical density measurements obtained at 495 nm.

TABLE F

The Effect of MS2B6 IgM on the Immunoassay for Ca125

| Additive | OD495* | % Inhibition |
|---|---|---|
| — | 0.27 | 0 |
| OC125, 0.5 ng | 0.25 | 8 |
| OC125, 5 ng | 0.12 | 50 |
| OC125, 50 ng | 0 | 100 |
| OC125, 500 ng | 0 | 100 |
| MS2B6, 5 μg | 0.27 | 0 |

*0.03 background subtracted

As little as 50 ng of unlabeled mouse monoclonal antibody OC125 completely inhibited binding of Ca125 standard to OC125 conjugated to test beads. There was no competition apparent in the Ca125 assay when up to 5 μg of MS2B6 IgM was added, indicating no significant cross-reactivity between OC125 and MS2B6 IgM.

EXAMPLE 10

Biodistribution Studies in Nude Mice

Female athymic nu/nu mice 6-8 weeks old were kept in a pathogen-free environment in filter-top cages. An intraperitoneal ovarian cancer model consisting of intraperitoneal growth of an adapted ovarian cancer cell line, 2774, was used. Injection of 10 × 10$^6$ line 2774 cells intraperitoneally uniformly causes death of the recipient nude mice within 25 to 40 days. Ascites, as well as intraperitoneal tumor growths on omentum, diaphragm and bowel, are routinely observed. In these experiments, mice were inoculated with line 2774 cells intraperitoneally, then on day 21 each received 2 μg $^{125}$I-labeled MS2B6 IgM intraperitoneally in 0.5 mL PBS. After 72 hours, the mice were sacrificed, and tissue specimens were obtained from tumor and normal tissues in each mouse. The specimens were rinsed in PBS, drained, weighed, and counted for $^{125}$I in a gamma counter. Statistical analysis of the difference in percent input cpm per gram among pairs of tumor and normal tissue from each mouse was performed using a paired t-test.

Tumor nodules from nude mice inoculated intraperitoneally with ovarian cancer cell line 2774 clearly expressed ADCA antigen, demonstrating positive staining of tumor nodules by biotin-labeled MS2B6 IgM and not by biotin-labeled control IgM. In vivo biodistribution studies were performed using intraperitoneal $^{125}$I-labeled MS2B6 IgM known to be active in antigen recognition based on radioimmunoblotting. The biodistribution results from two separate experiments using 3 mice each were combined and are summarized in Table G.

TABLE G $^{125}$I-Labeled MS2B6 IgM Biodistribution in an Ovarian Cancer Nude Mouse Model

| Tissue | % Input cpm/gm$^a$ | Tumor/Normal$^b$ Tissue Ratio | P value$^c$ |
|---|---|---|---|
| Tumor | 0.549 ± 0.121 | — | — |
| Skin | 0.137 ± 0.100 | 4.0 | 0.004 |
| Muscle | 0.084 ± 0.081 | 6.5 | 0.003 |
| Stomach | 0.114 ± 0.130 | 4.8 | 0.012 |
| Small Bowel | 0.176 ± 0.214 | 3.1 | 0.019 |
| Large Bowel | 0.176 ± 0.136 | 3.1 | 0.013 |
| Spleen | 0.098 ± 0.036 | 5.6 | 0.009 |
| Liver | 0.176 ± 0.093 | 3.1 | 0.011 |
| Kidney | 0.275 ± 0.224 | 2.0 | 0.048 |
| Heart | 0.100 ± 0.060 | 5.5 | 0.004 |
| Lung | 0.140 ± 0.068 | 3.9 | 0.009 |
| Vertebra | 0.097 ± 0.076 | 5.7 | 0.003 |
| Brain | 0.012 ± 0.009 | 45.8 | 0.005 |

$^a$Mean ± standard deviation (n = 6 except large bowel where n = 5).
$^b$Calculated from mean percent input cpm per gram data.
$^c$Two-tailed P Value calculated using paired t-test comparing tumor to normal tissue within each animal (n = 6 except large bowel where n = 5).

Substantial amounts of $^{125}$I labeled MS2B6 IgM were still present after 72 hr. in blood (0.5 to 2% input cpm per gram, mean 0.647±0.445) and ascites (2 to 6% input cpm per gram) in animals bearing intraperitoneal tumor growths. Contamination of tumor or normal tissue specimens by blood or ascites was minimized by careful rinsing in PBS prior to radioactivity counting. Tumor specimens retained significantly more $^{125}$I-labeled MS2B6 IgM than did normal tissue specimens, with a mean percent input cpm per gram value of 0.549±0.121 for tumor specimens removed from omental and subdiaphragmatic metastatic growths. Lower values were consistently observed among normal tissues, and these differences were statistically significant. Tumor-to-normal tissue ratios ranged from 2.0 (kidney) to 45.8 (brain). When the mean uptake for all normal tissues within each animal was compared to the tumor tissue uptake by paired t-testing, a two-tailed p value of 0.0046 was obtained.

EXAMPLE 11

$^{125}$I-MS2B6 MAb Radioimmunotherapy of Nude Mice

A pilot study was performed to indicate the potential efficacy of radioiodine-labeled MS2B6 in preventing death of nude mice injected intraperitoneally with ovarian cancer cell line 2774. The conditions were as described in Example 10 except that 10 μCi of $^{125}$I-labeled MS2B6 was injected intraperitoneally into each of 6 nude mice 3 days after they had received intraperitoneal injections of $10 \times 10^6$ cells per mouse of cell line 2774. Historical controls indicated that in the absence of a therapeutic effect, all mice would succumb to intraperitoneal tumor growth by day 40. Of the 6 mice in this experiment, none developed tumor. One mouse died at 3 weeks, of unknown cause, and was tumor-free. The other 5 mice continue to survive without evidence of intraperitoneal tumor, more than 84 days following cell line 2774 injection.

What is claimed is:

1. A method for determining the presence of adenocarcinoma having an ADCA antigen epitope in a patient comprising contacting a sample from the patient with an ADCA binding antibody and determining binding of the antibody with a component of the sample, the ADCA antigen having an epitope recognized by MS2B6 antibody and being a polypeptide selected from the group consisting of 38, 44, and 60 kD polypeptides, the ADCA antigen being an antigen of epithelial differentiation present in normal fallopian tube, endometrium, endocervix, bronchus, sweat duct, and large renal duct tissue.

2. The method of claim 1 wherein the sample is a fluid sample.

3. The method of claim 2 wherein the sample is a blood serum sample.

4. The method of claim 1 wherein the sample is a tissue sample.

5. The method of claim 1 wherein the antibody is a human monoclonal antibody.

6. The method of claim 1 wherein the antibody is MS2B6 IgM antibody.

7. A method for determined the presence of adenocarcinoma having an ADCA antigen epitope in a patient comprising contacting a blood serum sample from the patient with ADCA antigen or ADCA antiidiotype antibody and determining binding of ADCA antigen or ADCA antiidiotype antibody with antibody in the sample, the ADCA antigen having an epitope recognized by MS2 B6 antibody and being a polypeptide selected from the group consisting of 38, 44, and 60 kD polypeptides, the ADCA polypeptide being an antigen of epithelial differentiation present in normal fallopian tube, endometrium, endocervix, bronchus, sweat duct, and large renal duct tissue.

8. The MS2B6 hybridoma.

9. An antibody which binds preferentially with ADCA antigen, ADCA antigen having an epitope recognized by MS2B6 antibody and being a polypeptide selected from the group consisting of 38, 44, and 60 kD polypeptides, the ADCA polypeptide being an antigen of epithelial differentiation present in normal fallopian tube, endometrium, endocervix, bronchus, sweat duct, and large renal duct tissue.

10. An antibody of claim 9 which is a human monoclonal antibody.

11. As an antibody of claim 10, MS2B6 IgM antibody.

* * * * *

UNITED STATES PATENT AND TRADEMARK OFFICE
CERTIFICATE OF CORRECTION

PATENT NO. : 5,118,611
DATED : June 2, 1992
INVENTOR(S) : Lloyd H. Smith and Nelson N. H. Teng It is certified that error appears in the above-identified patent and that said Letters Patent is hereby corrected as shown below:

Column 6, line 27, before "ADCA" insert:

--The term 'ADCA antigen' is defined herein to be an adenocarcinoma cancer epitope or polypeptide including the epitope, which binds preferentially with MS2B6 hMAB.--

Column 20, line 38, delete "hu 123I" and insert --$^{123}$I--

Column 20, line 40, delete "and 131I-labeled" and insert --and $^{131}$I-labelled--.

Signed and Sealed this

Twenty-first Day of December, 1993

Attest:

BRUCE LEHMAN

*Attesting Officer*    *Commissioner of Patents and Trademarks*